United States Patent
Platzek et al.

(10) Patent No.: US 7,935,827 B2
(45) Date of Patent: May 3, 2011

(54) OPTICALLY ACTIVE, HETEROAROMATIC β-HYDROXY ESTERS AND PROCESSES FOR THEIR PREPARATION FROM β-KETO ESTERS AND PROCESSES FOR THE PREPARATION OF THESE β-KETO ESTERS

(75) Inventors: Johannes Platzek, Berlin (DE); Ludwig Zorn, Berlin (DE); Bernd Buchmann, Hohen Neuendorf (DE); Werner Skuballa, Berlin (DE); Orlin Petrov, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 12/338,179

(22) Filed: Dec. 18, 2008

(65) Prior Publication Data

US 2010/0248313 A1   Sep. 30, 2010

Related U.S. Application Data

(62) Division of application No. 11/027,671, filed on Jan. 3, 2005, now Pat. No. 7,626,035.

(30) Foreign Application Priority Data

Dec. 31, 2003 (DE) .................................. 103 61 794

(51) Int. Cl.
*C07D 215/14* (2006.01)
(52) U.S. Cl. ....................................................... 546/340
(58) Field of Classification Search .................... 546/340
See application file for complete search history.

(56) References Cited

U.S. PATENT DOCUMENTS

2003/0144533 A1   7/2003   Iwasaki et al.

FOREIGN PATENT DOCUMENTS

| DE | 10041470 | 2/2002 |
| WO | WO 97/12884 | 1/1997 |
| WO | WO 98/54350 | 12/1998 |
| WO | WO 00/58254 | 10/2000 |

OTHER PUBLICATIONS

Ratovelomanana-Vidal et al., "Enantioselective Hydrogenation of β-Keto Esters using Chiral Diphosphine-Ruthenium Complexes: Optimization for Academic and Industrial Purposes and Synthetic Applications," Advanced Synthesis and Catalysts, Jan. 21, 2003, pp. 261-274, vol. 345, No. 1/2, XP002326558, the whole document.
Database CA 'Online! D'Alo, F. et al., "N-Alkylalkanolamines of the benzo'b!thiophene series," 1965, Chemical Abstracts Service, Columbus, Ohio, US, XP002326559, retrieved from STN Database accession No. 1965:82375 RN: 1138-07-4, Benzo'b!thiophene-5-propionic acid,.beta.-oxo- abstract & Bollettino Chimico Farmaceutico, 1964, pp. 709-726, vol. 103, No. 10, CODEN:BCFAAI; ISSN: 0006-6648.

*Primary Examiner* — Taofiq A Solola
(74) *Attorney, Agent, or Firm* — Millen, White, Zelano & Branigan, P.C.

(57) ABSTRACT

The present invention relates to new optically active heteroaromatic β-hydroxy esters useful in the synthesis of epothilone derivatives, to certain compounds used to produce these intermediates, as well as to processes for their production.

9 Claims, No Drawings

OPTICALLY ACTIVE, HETEROAROMATIC β-HYDROXY ESTERS AND PROCESSES FOR THEIR PREPARATION FROM β-KETO ESTERS AND PROCESSES FOR THE PREPARATION OF THESE β-KETO ESTERS

This application is a divisional application of U.S. Application Ser. No. 11/027,671, filed on Jan. 3, 2005 now U.S. Pat. No. 7,626,035.

The invention relates to the subject matter characterized in the claims, i.e. novel optically active, heteroaromatic β-hydroxy esters and processes for the preparation as well as to their use as intermediate products in the total synthesis of epothilones and epothilone derivatives. The process for the production of the intermediate products yields products in high chemical purity, optical purity, in very good yields and allows an industrial-scale production.

Höfle et al. describes the cytotoxic effect of the natural substances epothilone A (R=hydrogen) and epothilone B (R=methyl)

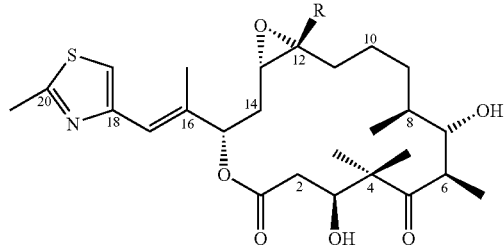

Epothilone A (R = H), Epothilone B (R = CH₃)

e.g. in Angew. Chem. 1996, 108, 1671-1673. Epothilones are representatives of a class of promising anti-tumor agents that were tested and found to be effective against a number of cancer lines. An overview of the syntheses for these compounds has been described by J. Mulzer in *Monatsh. Chem.* 2000, 131, 205-238. These agents have the same biological mode of action as paclitaxel and other taxanes (See for paclitaxel, D. G. I. Kingston, *Chem Commun.* 2001, 867-880), however, epothilones have also been shown to be active against a number of resistant cell lines (See S. J. Stachel et al., *Curr Pharmaceut. Design* 2001, 7, 1277-1290; K.-H. Altmann, *Curr. Opin. Chem. Biol.* 2001, 5, 424-431).

Due to their in vitro selectivity to breast and intestinal cell lines and their activity against P-glycoprotein forming, multi-resistant tumor lines, which is distinctly higher than that of Taxol, as well as their improved physical properties with respect to Taxol, e.g. a water solubility that is higher by the factor of 30, this new class of compounds is of special interest for the development of drugs for the treatment of malignant tumors.

In addition to the natural epothilones, the literature describes a large number of synthetically modified epothilone derivatives, including, inter alia, derivatives which contain an aromatic and/or heteroaromatic grouping in the 1-position instead of the methyl thiazole methyl vinyl side chains.

Epothilone derivatives with anellated aromatic heterocycles in the 1-position are also known in patent literature (Schering AG, WO 00/66589 and Novartis U.S. Pat. No. 6,387,927). Since these compounds are very potent antitumor agents, the development of an economic and efficient synthesis for producing them was of great interest. The intermediates of formulae II and III, representing some of the key compounds for the synthesis of this structural class, have already been described in the patent literature. The goal of the present invention is to provide a novel process for the production of novel intermediate compounds of general formula I for use in the synthesis of these epothilone derivatives:

wherein A stands for a bicyclic heteroaromatic residue of the formula:

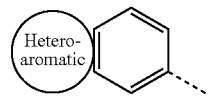

wherein "heteroaromatic" stands for a 5- or 6-membered heteroaromatic ring having up to 2 heteroatoms selected from oxygen, nitrogen or sulphur, which is optionally substituted with one or two substituents selected from alkyl, such as for example, methyl or ethyl; optionally protected hydroxyalkyl such as for example, TBDMS-OCH₂—; halo-alkyl such as for example, F—CH₂—; halogen such as Cl, F, or Br; or CN; and, wherein R stands for a straight-chain or branched, optionally saturated alkyl chain, which optionally contains 1-3 oxygen atoms, such as for example, methyl, ethyl, propyl, 2-propyl, n-butyl, tert-butyl, —CH₂CH=CH₂, —CH₂CH₂OCH₃, or —CH₂CH₂OCH₂CH₂OCH₃ group; or stands for a phenyl, cyclohexyl or benzyl radical.

A "bicyclic heteroaromatic residue" can, for example, stand for one of the following groups:

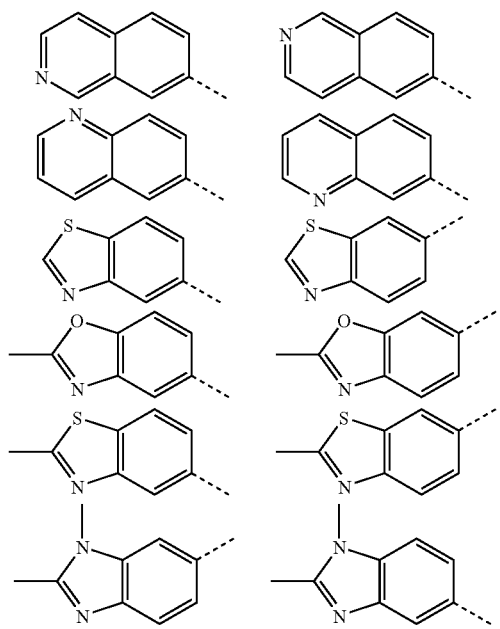

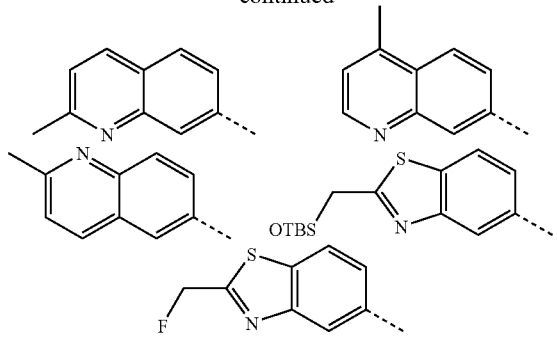

The compounds of general formula I are valuable intermediate compounds for the preparation of the intermediate compounds of general formulae II and III:

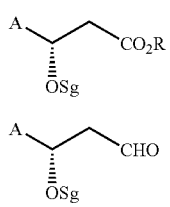

wherein Sg stands for an alcohol protecting group, such as for example TBDMS, THP, MEM, Mom, TROC, —CH$_2$—C$_6$H$_4$—OCH$_3$, or benzyl, with TBDMS being preferred. The compounds of general formula I are, therefore, also valuable in the total synthesis of epothilone derivatives.

Compounds of general formula II are prepared according to processes for the protection of secondary alcohols known to a person skilled in the art (See for example T. W. Greene, "Protecting groups in organic synthesis", John Wiley and Sons, Inc., edition 1999; P. J. Kociensky, "Protecting Groups", Georg Thieme Verlag Stuttgart, 1994).

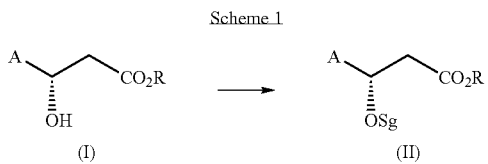

Compounds of the general formula III can either be prepared directly from the ester of formula II by means of a reduction with DIBAH (See Tetrahedron Lett. 1977, 3195-3198; Liebigs Ann. Chemie 1992, 145-158; JACS, 107, 1985, 3640-3645; Tetrahedron Lett. 31, 10, 1990, 1443-1446; Tetrahedron Lett. 31, 16, 1990, 2235-2238; Chem. Communications, 1999, 2049-2050; Bull. Chem. Soc. Jp. 66, 2, 1993, 523) or, in 2 stages, by first carrying out a reduction to alcohol and, subsequently, oxidizing to the aldehyde (See for reduction: Tetrahedron Lett. 58, 1, 2002, 61; JACS, 123, 34, 2001, 8420; Chem. Europ. J., 7, 24, 2001, 5286; Tetrahedron Asym. 12, 20, 2001, 2835; Org. Lett. 3, 20, 2001, 3149; JACS, 123, 13, 2001, 2946; Chem. Europ. J. 6, 18, 2000, 3313; and for oxidation: JACS, 123, 38, 2001, 9313; Org. Lett. 4, 11, 2002, 1879; JAGS, 123, 44, 2001, 10942; JOC, 66, 24, 2001, 8037; JOC, 66, 25, 2001, 8370; Tetrahedron Asym. 12, 20, 2001, 2835; Angewandte Chemie, 131, 2001, 3324; Org. Lett. 3, 22, 2001, 3549; Chem. Commun. 15, 2001, 1392).

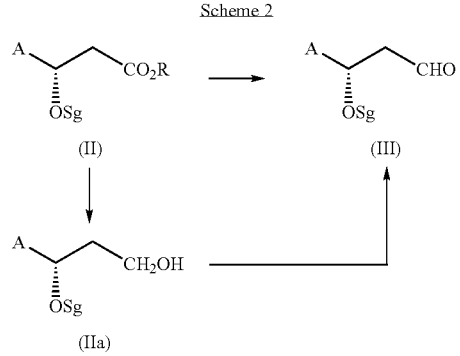

The methods presently existing in the literature for the preparation of the compounds of the general formulae II and III involve long synthesis sequences and poor total yields. In some cases, these processes also involve the use of technically expensive and complex processes such as cryo temperature reactions, irradiation, and very expensive raw materials and reagents.

The following syntheses for the synthesis of compounds of formula II are, for example, found in the literature:

1. Schering AG (WO 00/66589)
Number of steps: 5
Number of chromatography steps: 4

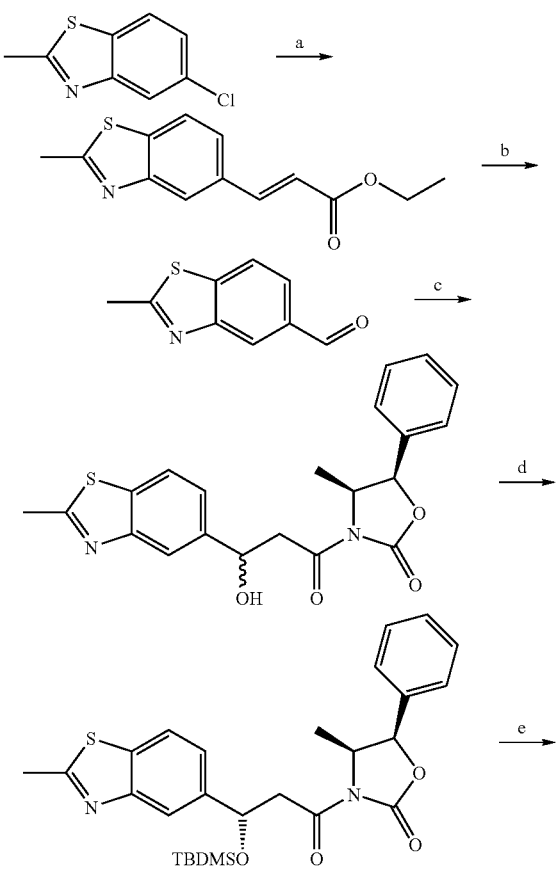

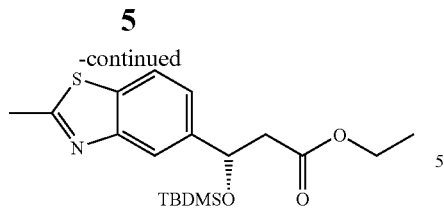

a) 1. NaI, NiBr$_2$, DMF, 150° C.; 2. ethyl acrylate, NEt$_3$, Tris(dibenzylidene acetone)-dipalladium, Tris(o-tolyl) phosphin, 150° C.
b) OsO$_4$, NaIO$_4$, THF/H$_2$O, room temperature
c) 3-Acetyl-(4R,5S)-4-methyl-5-phenyl-2-oxazolidinone, LiHMDS, THF or 3-bromoacetyl-(4R,5S)-4-methyl-5-phenyl-2-oxazolidinone, CrCl$_2$, THF, 40° C.
d) TBDMS-OTf, NEt$_3$, 0° C.
e) Ti(OEt)$_4$, EtOH, reflux This 5-stage synthesis starts from the very expensive chlorobenzotriazole compound and requires from the beginning the use of heavy metals such as nickel, palladium. The scaling-up of this reaction is additionally rendered more difficult by the high reaction temperature. In the second stage, the breaking of the double bond with osmium tetraoxide is carried out. Due to the high toxicity of this reagent, a transfer to a pilot plant scale is not feasible. The optical activity is achieved by means of an Evans aldol reaction, whereby the Evans auxiliary agent is used in excess (it must be produced in a two-stage sequence). The transfer of this process to an industrial scale is difficult, since expensive and partly very toxic raw materials are used. In addition, several chromatographic purifications are carried out.

2. NOVARTIS (U.S. Pat. No. 6,387,927 and PCT/EP99/10129)
   a)
   Number of steps: 4
   Number of chromatography steps: 4
   Total yield: Cannot be ascertained, since no individual yields are indicated.

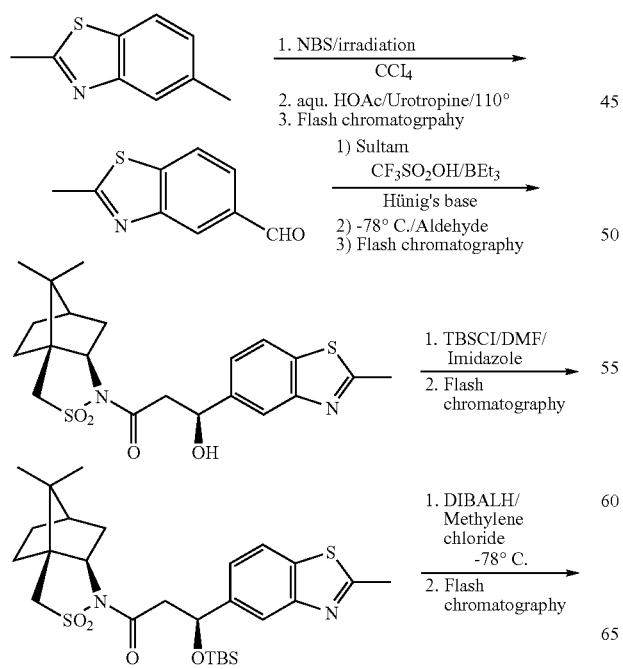

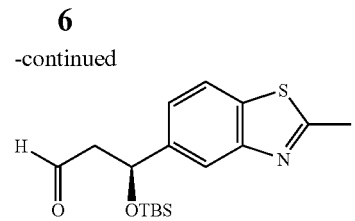

The first synthesis step is conducted by means of an irradiation (which is, in general unsuited for the implementation on an industrial scale) in the solvent carbon tetrachloride, a solvent which is no longer acceptable from an environmental protection perspective. Subsequently, the non-isolated brominated product is hydrolysed to aldehyde with a mixture of aqueous acetic acid and urotropine (110° C./80 min.). Purification is effected by means of flash chromatography on silica gel. The very expensive Oppolzer sultam (Tetrahedron Lett. 33, 2439, 1992) is stoichiometrically used for the asymmetric aldol reaction in the subsequent reaction and reacted in a process that takes place in a relatively complex fashion (via boron enolate). Purification is once again done, using flash chromatography. A reaction to silyl ether is subsequently carried out under standard conditions using TBDMS-Cl and another purification with chromatography is effected. The splitting off of the sultam residue is successful with DIBAH in dichloromethane at −78° C. The purification of the product takes place by means of chromatography on silica gel. This process involves several chromatography steps which result in additional costs and makes it difficult to transfer to an industrial scale. The use of the expensive sultam auxiliary agent is also a hurdle since it may be quite difficult to obtain this reagent in bulk amounts (>50 kg).

b)

Number of stages: 6

Number of chromatographies: 5

Total yield: Cannot be ascertained, since no individual yields are indicated.

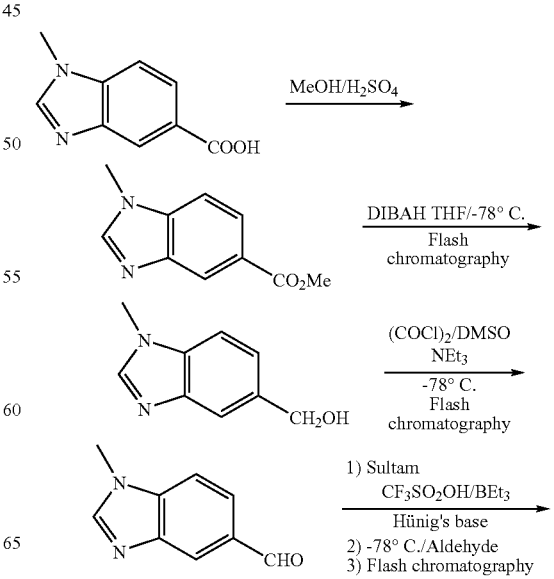

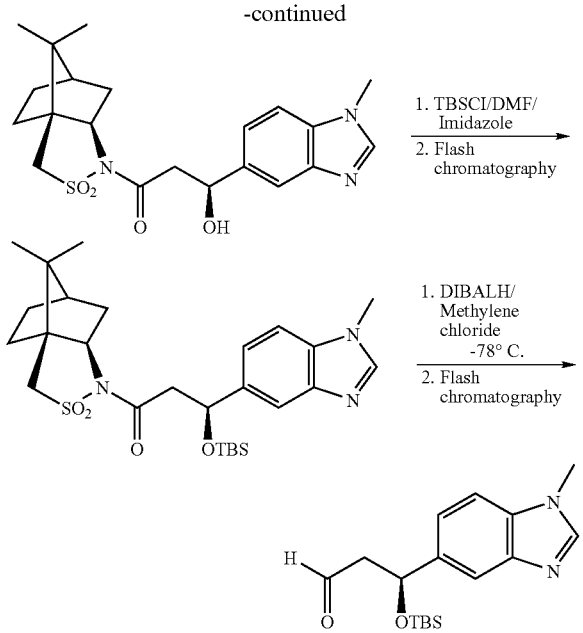

The key intermediate was synthesized starting from the methyl benzimidazole acid in a relatively long sequence. Upscaling is also rendered difficult by the fact that two low-temperature reactions are additionally used (DIBAH reduction and Swern oxidation).

Due to the complexity of these stages and the difficulties in scaling-up, there was a need for shorter and less expensive alternatives which offer the possibility of producing such intermediates on a scale of 100 kg.

These problems are avoided by the use of the processes described in the present invention, which allow us to obtain compounds of general formula I in a high total yield and high optical purity (>98% e.e.) from a starting material known in the literature in a very short sequence (2 steps). The conversion of compounds of general formula I to compounds of general formulae II and III is then easily carried-out as previously described in Schemes 1 and 2, i.e. using 1 or 2 further steps.

The preparation of compounds of general formula I is carried out by means of a chemical, microbiological or enzymatic reduction of a β-ketoester of general formula IV:

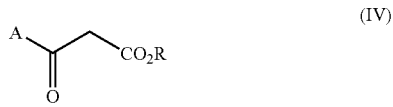

(IV)

wherein A and R, have the same meaning as indicated above under general formula I.

The reduction takes place in accordance with the process of β-ketoester reduction that is known to a person skilled in the art. The processes described in the experimental part serve as examples only.

a) Chemical Reduction

Examples of chemical reductions in the literature

1. Asymmetric Hydrogenations and Transfer Hydrogenations

M. Beller, C. Bolm "Transition Metals for Organic Synthesis", vol. 2, pages. 25 et seq., Wiley-VCH, 1998;

R. Noyori, Angew. Chemie 2001, 113, 40-75 (and the literature quoted in this article);

R. Noyori, Acc. Res. 1997, 30, 97-102; and

K. Murata, JOC 1999, 64, 2186-2187.

The catalyst used is also indicated in each case:

Ru(R-Xyl-P-Phos)($C_6H_6$)$Cl_2$

Wu, Jing; Chen, Hua; Kwok, Wai Him; Lam, Kim Hung; Zhou, Zhong Yuan; Yeung, Chi Hung; Chan, Albert S. C.; Tetrahedron Lett., 43, 8, 2002, 1539-1544.

[Ru(cod)($C_4H_7$)$_2$]/HBr ferrocenyl ligand

Ireland, Tania; Grossheimann, Gabriele; Wieser-Jeunesse, Catherine; Knochel, Paul; Angew. Chem. Int. Ed., 38, 21, 1999, 3212-3215; Angew. Chem., 111, 1999, 3397-3400.

(R)-MeO-BIPHEP-RuBr$_2$

Ratovelomanana-Vidal, Virginie; Genet, Jean-Pierre; JORCAI; J. Organomet. Chem. 567, 1-2, 1998, 163-172; Genet, J. P.; Ratovelomanana-Vidal, V.; Cano de Andrade, M. C.; Pfister, X.; Guerreiro, P.; Lenoir, J. Y., Tetrahedron Lett., 36, 27, 1995, 4801-4804.

(R)-Diamo-BINAPRuBr$_2$

Guerreiro, Patricio; Ratovelomanana-Vidal, Virginie; Genet, Jean-Pierre; Dellis, Philippe, Tetrahedron Lett., 42, 20, 2001, 3423-3426.

(+)-[(4,4'-PPh$_2$-2,2',5,5'-Me-3,3'-bithiophene)RuCl($C_6H_6$)] Cl HBF$_4$

Benincori, Tiziana; Cesarotti, Edoardo; Piccolo, Oreste; Sannicolo, Franco; J. Org. Chem., 65, 7, 2000, 2043-2047.

(−)-2,2'-bis(diphenylphosphino)-4,4',6,6'-tetramethyl-3,3'-bibenzo<b>thiophene-RuCl$_2$ Benincori, Tiziana; Brenna, Elisabetta; Sannicolo, Franco; Trimarco, Licia; Antognazza, Patrizia; Cesarotti, Edoardo; J. Chem. Soc. Chem. Commun., 6, 1995, 685-686.

(+)-3-[(2-Ph$_2$P-5-MeO)$C_6H_3$]-2-(Ph$_2$P)naphtho[2,1-b]thiophene

Sannicolo, Franco; Benincori, Tiziana; Rizzo, Simona; Gladiali, Serafino; Pulacchini, Sonia; Zotti, Gianni; Synthesis, 15, 2001, 2327-2336.

(+)-3-[2-(Ph$_2$P)—$C_6H_4$]-2-(Ph$_2$P)naphtho[2,1-b]thiophene Ru(II)

Benincori, Tiziana; Gladiali, Serafino; Rizzo, Simona; Sannicolo, Franco; J. Org. Chem., 66, 17, 2001, 5940-5942.

(R,R)-1,3-dicyclohexyl-1,3-propanediol cyclic sulfate [($C_6H_6$)RuCl$_2$]$_2$

Marinetti, Angela; Jus, Sebastien; Genet, Jean-Pierre; Ricard, Louis; J. Organomet. Chem., 624, 1-2, 2001, 162-166.

RuCl$_3$+(S)-MeO-BIPHEP

Madec, J.; Pfister, X.; Phansavath, R; Ratovelomanana-Vidal, V.; Genet, J.-P.; Tetrahedron, 57, 13, 2001, 2563-2568.

(−)-(6,6'-O(CH$_2$)$_4$O-biphenyl-2,2'-diyl)bis(diphenylphosphine) [Ru($C_6H_6$)Cl$_2$]$_2$ Zhang, Zhaoguo; Qian, Hu; Longmire, James; Zhang, Xumu; J. Org. Chem., 65, 19, 2000, 6223-6226.

[Ru(cod)($C_4H_7$)$_2$]/HBr ferrocenyl ligand

Ireland, Tania; Grossheimann, Gabriele; Wieser-Jeunesse, Catherine; Knochel, Paul; Angew. Chem. Int. Ed., 38, 21, 1999, 3212-3215; Angew. Chem., 111, 1999, 3397-3400.

[RuCl$_2$(p-cymene)]$_2$(1S,2R)-ephedrine i-PrOK

Everaere, Kathelyne; Carpentier, Jean-Francois; Mortreux, Andre; Bulliard, Michel; Tetrahedron: Asymmetry, 10, 24, 1999, 4663-4666.

(−)-[4,4'-PPh$_2$-2,2',5,5'-Me-3,3'-bithiophene]RuCl$_2$

Marinetti, Angela; Genet, Jean-Pierre; Jus, Sebastien; Blanc, Deiphine; Ratovelomanana-Vidal, Virginie; Chem. Europ. J., 5, 4, 1999, 1160. 1165.

<Ru(p-cymene)Cl$_2$>2, (1S,2R)-(+)-ephedrine, i-PrOK

Everaere, Kathelyne; Carpentier, Jean-Francois; Mortreux, Andre; Bulliard, Michel; Tetrahedron: Asymmetry, 9, 17, 1998, 2971-2974.
1,2-bis(t-butylmethylphosphino)ethane, hydrogen RuBr$_2$
Yamano, Toru; Taya, Naohiro; Kawada, Mitsuru; Huang, Taisheng; Imamoto, Tsuneo; Tetrahedron Lett., 40, 13, 1999, 2577-2580.
<(−)-2,2'-bis(diphenylphosphino)-4,4',6,6'-tetramethyl-3,3'-ibenzo<b>thiophene>RuCl$_2$
Benincori, Tiziana; Brenna, Elisabetta; Sannicolo, Franco; Trimarco, Licia; Antognazza, Patrizia; et al.; J. Org. Chem., 61, 18, 1996, 6244-6251.
RuBr$_2$<(R)-binap>
Noyori, R.; Ohkuma, T.; Kitamura, M.; Takaya, H.; Sayo, N.; et al.; J. Amer. Chem. Soc., 109, 19, 1987, 5856-5858.
Ru(R-Tol-P-Phos)(C$_6$H$_6$)Cl$_2$
Wu, Jing; Chen, Hua; Zhou, Zhong-Yuan; Yeung, Chi Hung; Chan, Albert S. C.; Syn. Lett., 2001, 1050-S1054.
RuCl$_2$[(−)-N,N-Me2-3,3'-bis(Ph$_2$P)-2,2'-biindole]
Benincori, Tiziana; Piccolo, Oreste; Rizzo, Simona; Sannicolo, Franco; J. Org. Chem., 65, 24, 2000, 8340-8347.
(R)-Me-Duphos-RuBr$_2$
Genet, J. P.; Ratovelomanana-Vidal, V.; Cano de Andrade, M. C.; Pfister, X.; Guerreiro, P.; Lenoir, J. Y.; Tetrahedron Lett., 36, 27, 1995, 4801-4804.
[NH$_2$Me$_2$][{RuCl[(R)-segphos]}$_2$(μ-Cl)$_3$]
Saito, Takao; Yokozawa, Tohru; Ishizaki, Takero; Moroi, Takashi; Sayo, Noboru; Miura, Takashi; Kumobayashi, Hidenori; Adv. Synth. Catal., 343, 3, 2001, 264-268.

The asymmetric hydrogenation is carried out in solvents such as methanol, ethanol, trifluoroethanol, THF, 2-methyl-THF, dichloromethane and mixtures of these solvents. The reaction temperature is from 0 to 100° C. and the reaction times are from 3 to 72 hours. The catalyst is added with 0.01 to 5 mole % (based on the substrate). It proved to be useful in some cases to add 0.1 to 30% of water in the case of solvents miscible with water. Sometimes it is advantageous to add 0.01 to 5 mole eq. (based on the substrate) of an inorganic or organic acid, such as HCl, H$_3$PO$_4$, H$_2$SO$_4$, acetic acid, methane sulfonic acid, p-TsOH, phenyl sulfonic acid, camphor sulfonic acid. Hydrogenation takes place at temperatures of 0° C. to 100° C. and hydrogen pressures of 1 to 270 bar.

2. Asymmetric Reduction with Complex Hydrides
LiBH$_4$, (R,R)—N,N'-dibenzoylcystine, t-BuOH
Soai, Kenso; Yamanoi, Takashi; Hikima, Hitoshi; Oyamada, Hidekazu; J. Chem. Soc. Chem. Commun., 3, 1985, 138-139.
Tartaric acid, NaBH$_4$
J. Chem. Soc. Perkin Trans. 1, 1990, 1826.

b) Microbiological Reduction
In general, the use of microorganisms of the following species:
baker's yeast, *Brettanomyces bruxellensis, Candida albicans, Candida boidinii, Candida gropengiesseri, Candida guilliermondii, Candida kefyr, Candida pini, Candida rugosa, Candida solani, Candida tropicalis, Candida utilis, Candida valida, Clostridium beijerinckii, Clostridium pasteurianum, Cryptococcus laurentii, Cryptococcus macerans, Debaryomyces hansenii, Debaryomyces kloeckeri, Debaryomyces nicotianae, Debaryomyces vini, Endomycopsis fibuliger, Hanseniaspora guilliermondii, Hanseniaspora osmophila, Hanseniaspora uvarum, Hansenula capsulata, Hansenula holstii, Hansenula polymorpha, Hansenula saturnus, Hansenula silvicola, Issatchenkia orientalis, Kloeckera apiculata, Kloeckera corticis, Kloeckera javanica, Kloeckera sp., Kluyveromyces lactis, Kluyveromyces marxianus Kluveromyces sphaerica, Lactobacillus kefir, Nadsonia fulvescens, Octosporomyces octosporus, Pichia anomala, Pichia cactophila, Pichia farinosa, Pichia fermentans, Pichia holstii, Pichia jadinii, Pichia membranaefaciens, Pichia pijperi, Pichia silvicola, Pichia subpelliculosa, Pichia wickerhamii, Rhodotorula flava, Rhodotorula glutinis, Rhodotorula minuta* var. *minuta, Saccharomyces acidificans, Saccharomyces bailii, Saccharomyces bayanus, Saccharomyces carlsb.* strain *Herrliberg, Saccharomyces carisbergensis, Saccharomyces cerevisiae, Saccharomyces chevalieri, Saccharomyces exiguus, Saccharomycopsis fibuligera, Saccharomyces paradoxus, Saccharomyces pastorianus, Saccharomyces pastorianus* formerly *Saccharomycopsis capsularis, Saccharomyces* sp., *Schizosaccharomyces pombe, Schizosaccharomyces octosporus, Sporobolomyces coralliformis, Sporobolomyces salmonicolor, Torulopsis pinus, Trigonopsis varabilis, Tremella fuciformis, Waltomyces lipofer, Zygosaccharomyces fermentati* or *Zygosaccharomyces rouxii*, are used for the microbiological reduction. Preferred is the *Pichia wickerhamii* microorganism.

Literature:
Bardot, Valerie; Besse, Pascale; Gelas-Miahle, Yvonne; Remuson, Roland; Veschambre, Henri; Tetrahedron: Asymmetry, 7, 4, 1996, 1077-1088.
Bhalerao, U. T.; Chandraprakash, Y.; Babu, R. Luke; Fadnavis, N. W.; Synth. Commun., 23, 9, 1993, 1201-1208.
Chenevert, Robert; Fortier, Genevieve; Rhlid, Rachid Bel; Tetrahedron, 48, 33, 1992, 6769-6776.
Mochiziki, Naoki; Sugai, Takeshi; Ohta, Hiromichi; Biosci. Biotechnol. Biochem., 58, 9, 1994, 1666-1670.
Kumar, Ashok; Ner, Dilip H.; Dike, Suneel Y.; Tetrahedron Lett., 32, 16, 1991, 1901-1904.
Mochiziki, Naoki; Sugai, Takeshi; Ohta, Hiromichi; Biosci. Biotechnol. Biochem., 58, 9, 1994, 1666-1670.
Manzocchi, Ada; Casati, Rosangela; Fiecchi, Alberto; Santaniello, Enzo; J. Chem. Soc. Perkin Trans. 1, 1987, 2753-2758.

c) Enzymatic Reduction
Literature:
Deol, B. S. et al.; Aust. J. Chem., 29, 1976, 2459-2467.
Ema, Tadashi; Moriya, Hiroyuki; Kofukuda, Toru; Ishida, Tomomasa; Maehara, Kentaro; Utaka, Masanori; Sakai, Takashi; J. Org. Chem., 66, 25, 2001, 8682-8684.

However, the use of microbiological reductions with yeasts and/or modified yeasts and the processes for asymmetric hydrogenation and transfer hydrogenation relying on Noyori are preferred.

The methods described above also allow for the preparation of the antipode of compounds of general formula I, namely Ia:

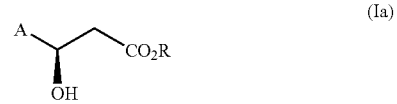

(Ia)

The β-ketoesters of the general formula IV

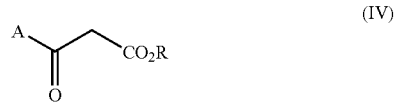

(IV)

wherein A and R have the same meaning as indicated above under general formula I, can be prepared using known methods by reacting activated acid derivatives of the general formula V with malonic acid ester derivatives of the general formula VI:

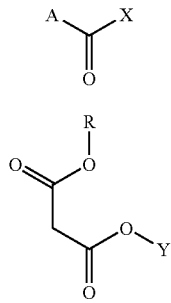

(V)

(VI)

Wherein X stands for a chlorine, bromine, 4-nitrophenol or the imidazoyl residue, R has the same meaning as indicated above under general formula I, and Y stands for hydrogen, Li, Na, K or Mg/2 or a silyl protective group such as trimethylsilyl.

Examples of β-ketoester syntheses are described in the literature:

Synthesis 1993(3), 290/292; Med. Chem. 1985, 28(12), 1864; Tetrahedron Lett. 1984, 25, 5681; J. Heterocycl. Chem. 1996, 33(4), 1407; Org. Prep. Proceed. 1997, 29(2), 231; Arch. Pharm. (Weinheim, Ger.) 1997, 330(3), 63-66; Tetrahedron Lett. 1994, 35(50), 9323; Tetrahedron Lett. 1994, 35(50), 9323; Synthesis, 1993, 290; J. Chem. Educ. 1983, Vol. 60, No. 3, 244; Tetrahedron Lett. 30, 1992, 5983; Synthesis, 1998, S. 633; Chem. Commun. 1999, 1113; Tetrahedron, 1985, Vol. 41, 5229; Angewandte Chemie 1979, S. 76; Tetrahedron Lett. 35, 50, 1994, 9323-9326.

The starting products of general formulae V and VI are known in the literature and partly commercially available or can be prepared in accordance with methods well known to a person skilled in the art.

The following examples are given: J. Chem. Soc. 1947, 437, 441; JACS 1939, 61, 183; Bioorg. Med. Chem. Lett. 1999, 2583; Chem. Commun. 2, 2002, 180; Chem. Ber. 23, 1890, 2272; U.S. Pat. No. 2,647,050 (1949 Du Pont); Zh. Obshch. Khim., 26, 1956, 3388, 3390; J. Chem. Soc. 1949, 355, 361; Synthetic Commun. 26, 19, 1996, 3535-3542; J. Chem. Soc. 1966, 1980-1983; JACS 75, 1953, 6237; JACS, 75, 1953, 2770; J. Chem. Soc. Perkin Trans. 1974, 903, 908; Zh. Obshch. Khim., 32, 1962, 1581; Chem. Pharm. Bull., 14, 1966, 375, 381.

Most of the processes for β-ketoesters that are described in literature have, however, the disadvantage that large amounts of by-products such as the compounds A and B

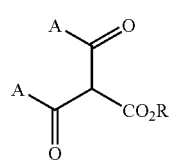

(A)

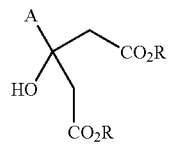

(B)

are formed, which interferes with the quantitative crystallization of the desired product.

Even in the preparation of β-ketoesters described by X. Wang in Tetrahedron Letters, vol. 35, 50, 1994, 9323, in which DBU (diazobicycloundecane) is used in the deprotonation step, large amounts of the byproducts A and B are observed in scaling-up.

A further object of the present invention is to provide for a novel process which uses tert-butylates and/or tert-amylates for deprotonation, which avoids the formation of by-products A and B.

The following one-pot sequence (Scheme 3) starting from the acids of the general formula VII:

(VII)

wherein A has the same meaning as indicated above under general formula I, proved to be especially advantageous.

Scheme 3

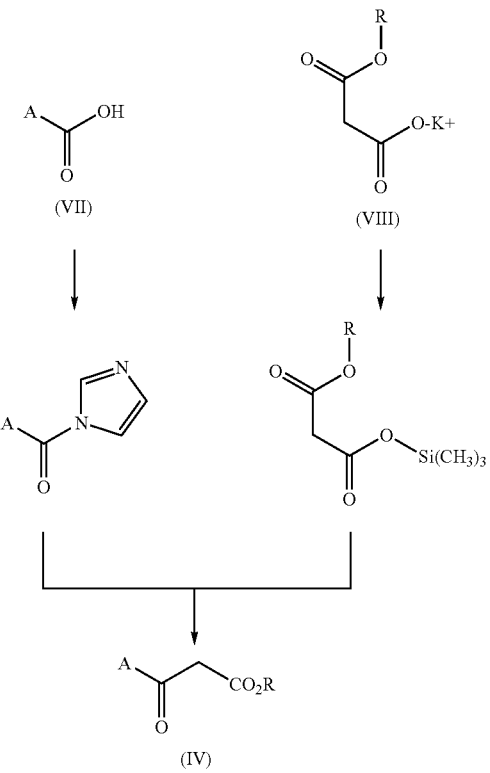

Starting from the acid of the general formula VII, the imidazolide is prepared according to methods known to a person skilled in the art. More specifically, N,N-carbodiimidazole (Staab's reagent) in a non-protic solvent such as THF, 2-methyl-THF, dioxane, dichloromethane, toluene, dimethylformamide, optionally with the addition of dimethylaminopyridine (0.001-3 eq.) is preferably reacted with the acid VII at temperatures from 0-70° C. for 1-10 hours.

After the completed reaction, the imidazolide can be isolated. However, it is preferred to add the obtained solution to a second solution (preparation: reaction of malonic acid semiester potassium salt VIII in an aprotic solvent such as THF, 2-methyl-THF, dioxane, dichloromethane, toluene, dimethylformamide with trimethylsilylchloride to silylester, reaction time 1-10 hours at temperatures of −10 to 30° C.). Subsequently, deprotonation takes place with 1-4 eq. of a base such as potassium tert-butylate, sodium tert-butylate, lithium tert-butylate, potassium-O—CH$_2$C(CH$_3$)$_3$ (in the case of reactions on an industrial scale, the inorganic bases are preferably added, dissolved in a solvent such as THF, at temperatures of from −10 to +30° C., subsequent stirring time 10 minutes to 5 hours). The addition time is 30 minutes to 10 hours, and it is possible to meter a cold solution (0° C.) or a solution having a temperature of up to 70° C. After the addition has been completed, renewed stirring is carried out for 1 to 24 hours, preferably at temperatures of from 0 to 50° C.

The addition 1 to 5 mole equivalents of lithium chloride or lithium bromide prior to the addition of the base proved to be advantageous in some cases in order to improve the stirrability of the batch. This stirrability is of special importance in view of scaling-up to the pilot plant, i.e. industrial scale which could involve the risk of breaking the stirrer.

Water is added for reprocessing the reaction solution, adjustment of the pH value is carried out with a mineral acid such as HCl, sulphuric acid or phosphoric acid (pH 1.5-8) and the product is isolated by means of extraction (e.g. acetic acid ethyl ester, MTB, etc.). After drying of the organic phase over a desiccant (MgSO$_4$ or Na$_2$SO$_4$) or by means of azeotropic distillation (pilot plant), redistillation to the final solvent used for crystallization is carried out.

Since the ketoesters of general formula IV are obtained as crystalline solids, they can be easily purified by means of crystallization. Isolation is carried out by means of filtration, rewashing with the previously-used solvent and subsequent drying (vacuum or circulating air).

The β-ketoesters of general formula IV prepared as described above are obtained in a high yield (approx. 91-93%, starting from the acid) and purity.

The sodium and/or lithium salt can also be used instead of the potassium salt of the malonic acid semi-ester.

For the sake of comparison of the novel process of the present invention with examples from the previously-mentioned patent literature, it can be said that starting from acids known in the literature, the respectively required key intermediates can be prepared with a few steps in high purity and high yields (without chromatography).

The synthesis according to the invention can be further illustrated by means of the following two examples:

1st EXAMPLE

Chiral methylbenzimidazole aldehyde

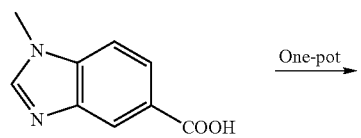

2nd EXAMPLE

Chiral methylbenzothiazole ethyl ester

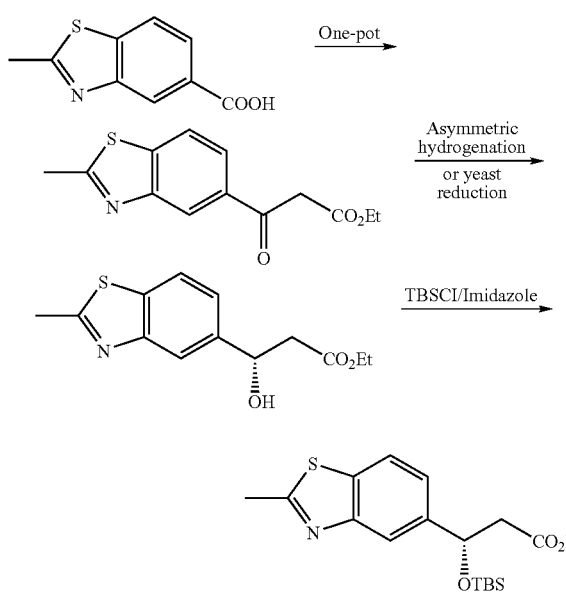

The reactions described above are preferably carried-out under conditions analogous to those given in the following examples. The following examples are intended to illustrate the invention without being intended to restrict the scope of the invention:

EXAMPLES

β-Ketoester Synthesis (General Specification for the Preparation of Compounds of General Formula IV)

Preparation of Solution A:

260 mmole of the acid (A-COOH; compound of the general formula Formel VII) are suspended in 300 ml of THF at room temperature and 950 mg of dimethylaminopyridine are added. A solution consisting of 285 mmole 1,1-carbodiimidazole in 500 ml of THF are added dropwise at 40° C. and stirring is carried out at 50° C. for 7 hours.

Preparation of Solution B:

777 mmole of malonic acid semiester potassium salt (ROOC—CH$_2$—COOK; compound of the general formula VIII) are suspended in 250 ml of THF at 20° C. Subsequently, 777 mmole of chlorotrimethylsilane are added dropwise and stirring is again carried out for 7 hours. Cooling to 0° C. is carried out, 1000 mmole of lithium chloride are optionally added and a solution of 1.365 mole of potassium tert. butylate, dissolved in 300 ml of THF is added dropwise (under counter-cooling). Subsequently, stirring is carried out again for 30 minutes at 0° C.

Solution A with a temperature of 50° C. is added to solution B dropwise under vigorous stirring within 30 minutes (the temperature is kept at 0° C. by means of counter-cooling). After the addition has been completed, stirring is carried out at 0° C. for 30 minutes and subsequently at 20° C. for 15 hours.

Processing:

1000 ml of acetic acid ethyl ester is added and a pH of 2 is adjusted by adding 920 ml of 2N hydrochloric acid (when doing so, the solution clears up, two phases are formed). The organic phase is separated and washed twice with 750 ml of saturated aqueous sodium hydrogen carbonate solution. Subsequently, the organic phase is washed with 500 ml of saturated sodium chloride solution. After drying over a desiccant (sodium sulfate or magnesium sulfate) 7 g of activated carbon are added and stirred is carried out at 20° C. for 30 minutes. After filtering off of the activated carbon, the filtrate is concentrated in vacuo and then the solvent for the final crystallization is added.

Recrystallization is carried out from the respectively most advantageous solvent (cf. table). Mostly, further crystal fractions can be obtained from the mother liquors. The product is dried in a vacuum-drying cabinet or under circulating air (20 to 50° C.).

The following examples were implemented in accordance with the process described above (product=compound of the general formula IV):

Example 1

| Product | Yield % of the theory | Solvent of crystallization | Elementary analysis Found/calc. | |
|---|---|---|---|---|
| (structure) | 91 | Cyclohexane | C | 69.51/69.12 |
| | | | H | 5.58/5.39 |
| | | | N | 5.64/5.76 |

Example 2

| Product | Yield % of the theory | Solvent of crystallization | Elementary analysis Found/calc. | |
|---|---|---|---|---|
| (structure) | 91 | Cyclohexane/ MTBE | C | 67.90/68.11 |
| | | | H | 5.05/4.84 |
| | | | N | 6.00/6.11 |

Example 3

| Product | Yield % of the theory | Solvent of crystallization | Elementary analysis Found/calc. |
|---|---|---|---|
| 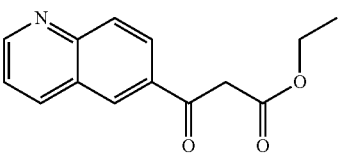 | 92 | Cyclohexane | C 68.89/69.12<br>H 5.53/5.39<br>N 5.58/5.76 |

Example 4

| Product | Yield % of the theory | Solvent of crystallization | Elementary analysis Found/calc. |
|---|---|---|---|
| 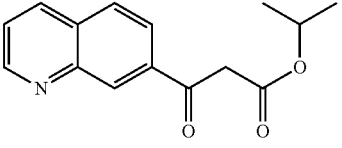 | 92 | Heptane/acetic acid ethyl ester | C 69.88/70.02<br>H 6.10/5.88<br>N 5.51/5.44 |

Example 5

| Product | Yield % of the theory | Solvent of crystallization | Elementary analysis Found/calc. |
|---|---|---|---|
| 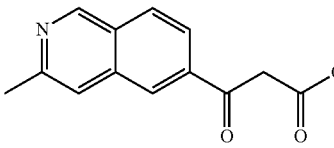 | 91 | Cyclohexane | C 70.21/70.02<br>H 6.09/5.88<br>N 5.31/5.44 |

Example 6

| Product | Yield % of the theory | Solvent of crystallization | Elementary analysis Found/calc. |
|---|---|---|---|
| 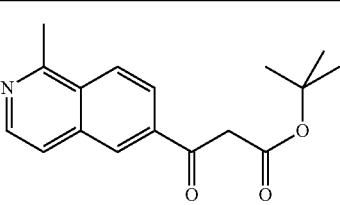 | 92 | Cyclohexane | C 71.70/71.56<br>H 6.85/6.71<br>N 4.80/4.91 |

Example 7

| Product | Yield % of the theory | Solvent of crystallization | Elementary analysis Found/calc. | |
|---|---|---|---|---|
| 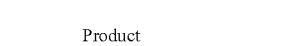 | 91 | Cyclohexane | C<br>H<br>N | 69.85/70.02<br>6.05/5.88<br>5.37/5.44 |

Example 8

| Product | Yield % of the theory | Solvent of crystallization | Elementary analysis Found/calc. | |
|---|---|---|---|---|
| 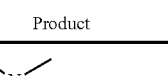 | 93 | Cyclohexane/ MTBE | C<br>H<br>N | 61.90/62.06<br>5.35/5.21<br>11.91/12.06 |

Example 9

| Product | Yield % of the theory | Solvent of crystallization | Elementary analysis Found/calc. | |
|---|---|---|---|---|
| | 93 | Cyclohexane | C<br>H<br>N | 63.59/63.40<br>5.90/5.73<br>11.21/11.38 |

Example 10

| Product | Yield % of the theory | Solvent of crystallization | Elementary analysis Found/calc. | |
|---|---|---|---|---|
| | 92 | Cyclohexane | C<br>H<br>N | 63.31/63.15<br>5.49/5.30<br>5.51/5.66 |

Example 11

| Product | Yield % of the theory | Solvent of crystallization | Elementary analysis Found/calc. | |
|---|---|---|---|---|
| 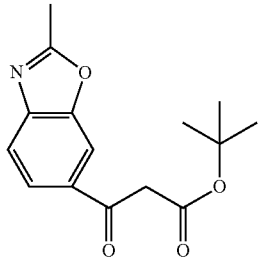 | 93 | Cyclohexane | C<br>H<br>N | 65.35/65.44<br>6.39/6.22<br>4.98/5.09 |

Example 12

| Product | Yield % of the theory | Solvent of crystallization | Elementary analysis Found/calc. | |
|---|---|---|---|---|
| 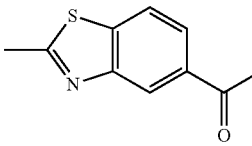 | 93 | Hexane | C<br>H<br>N<br>S | 59.41/59.30<br>5.12/4.98<br>5.21/5.32<br>12.03/12.18 |

Example 13

| Product | Yield % of the theory | Solvent of crystallization | Elementary analysis Found/calc. | |
|---|---|---|---|---|
| 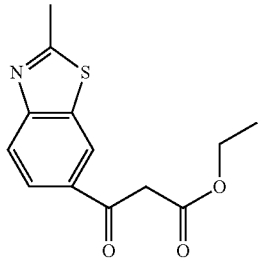 | 91 | Cyclohexane | C<br>H<br>N<br>S | 59.17/59.30<br>5.18/4.98<br>5.18/5.32<br>12.01/12.18 |

Example 14

| Product | Yield % of the theory | Solvent of crystallization | Elementary analysis Found/calc. | |
|---|---|---|---|---|
| 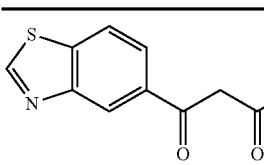 | 93 | Hexane | C<br>H<br>N<br>S | 58.01/57.82<br>4.58/4.45<br>5.71/5.62<br>12.78/12.86 |

Example 15

| Product | Yield % of the theory | Solvent of crystallization | Elementary analysis Found /calc. | |
|---|---|---|---|---|
| 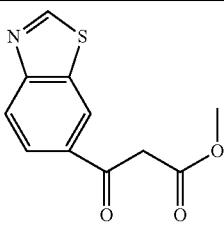 | 91 | Cyclohexane | C<br>H<br>N<br>S | 56.27/56.16<br>4.02/3.86<br>5.89/5.95<br>13.57/13.63 |

The above-mentioned compounds of general formula IV illustrated in examples 1 to 15 all form part of the subject matter of the present invention.

In the following, the processes used for asymmetric reduction are in each case generally described:

Chiral Reduction Methods

A) General Description for a Microbiological Reduction

A 500 ml Erlenmeyer flask which contains 100 ml of a nutrient solution of 5% glucose and 2% corn steep liquor (pH 6.0-6.5), which was sterilized in an autoclave at 121° C. for 20 minutes, is inoculated with an oblique tube culture of the *Pichia wickerhamii* strain (IFO 1278) and shaken on a rotation shaker at 28° C. for 48 hours. Two 2 l Erlenmeyer flasks are inoculated with 50 ml each of this culture, which are charged with 500 ml of sterile medium of the same composition as described for the culture.

After a growth phase of 6 hours at 28° C., a solution of 5 mmole β-ketoester of the general formula IV in 15 ml DMF is added to each Erlenmeyer flask. Subsequently, shaking is continued at 28° C.

After a contact time of 114 hours, the combined culture broths are extracted twice with 1 l of acetic acid ethyl ester. The combined organic phases are dried, filtered over Celite (or a silica gel layer) and concentrated in vacuo. The residue is recrystallized from a solvent of choice.

B) Asymmetric Hydrogenation with Chiral Metal Catalysts

The asymmetric hydrogenation was carried out in accordance with methods described in literature. If an acid was used for hydrogenation, this is indicated in the examples.

Processing of the hydrogenation batches: Concentration by evaporation is carried out, the residue is taken up with an nonpolar solvent (e.g. dichloromethane, MTBE) and filtering off is carried out over a short silica gel layer. The filtrate is evaporated to dryness in vacuo and the residue is recrystallized from a suitable solvent.

C) Example of a Transfer Hydrogenation 1 mmole of dichloro(pentamethylcyclopentadienyl) rhodium(III) dimer is added to a solution consisting of 4 mmole of (R,R)-Tos-DPEN in 1 l of isopropanol under a nitrogen atmosphere and stirred 20 minutes at 80° C. until an orange red, homogeneous solution is obtained. Subsequently, 100 ml of potassium isopropylate (0.12 m solution=120 mmole) are added. Then 200 mole of β-ketoester of the general formula IV (dissolved in 500 ml of isopropanol) are added and stirring is carried out at 50° C. (1 to 20 hours) and the course of the reaction is pursued by means of DC.

After completion of the reaction, the reaction mixture is evaporated to dryness in vacuo and the residue is filtered over a layer of silica gel (solvent: mixtures of hexane/acetic acid ethyl ester). The reaction mixture is evaporated to dryness in vacuo and recrystallization from a suitable solvent is carried out.

D) Asymmetric Reduction with Complex Hydrides ($NaBH_4$/$LiBH_4$)

Reductions with the chiral auxiliary component (R,R')—N,N'-dibenzoylcysteine are carried out in accordance with the specification from J. Chem. Soc. Chem. Commun. 1985, 138.

Reductions with the chiral auxiliary component (2R,3R)-tartaric acid are carried out in accordance with the specification from J. Chem. Soc. Perkin Trans. 1, 1990, 1826.

Example 16

Reduction method: C
e.e. of the product after crystallizaton: >98%
Literature: R. Noyori, Acc. Res. 1997, 30, 97-102
K. Murata, JOC 1999, 64, 2186-2187

| Product | Yield % of the theory | Solvent of crystallization | Elementary analysis Found/calc. | |
|---|---|---|---|---|
| 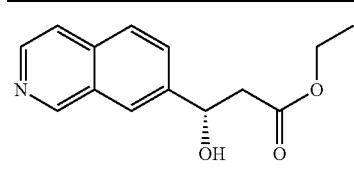 | 95 | Cyclohexane/ MTBE | C<br>H<br>N | 68.41/68.56<br>6.31/6.16<br>5.63/5.71 |

Example 17

Reduction method: B
Solvent: methanol
Pressure: 1200 psi
Temperature: 25° C.
Reaction time: 14 hours
e.e. of the product after crystallization: >98%
Literature: JAGS, vol. 121, No. 30, 1999, page 7061 (compound 43)

| Product | Yield % of the theory | Solvent of crystallization | Elementary analysis Found/calc. | |
|---|---|---|---|---|
| [isoquinoline-6-yl (S)-3-hydroxy-methyl ester structure] | 94 | Cyclohexane/ MTBE | C<br>H<br>N | 67.47/67.52<br>5.78/5.67<br>5.89/6.06 |

Example 18

Reduction method: B
Solvent: ethanol
Pressure: 1300 psi
Temperature: 40° C.
Reaction time: 18 hours
e.e. of the product after crystallization: >99%
Literature: as indicated in example 17

| Product | Yield % of the theory | Solvent of crystallization | Elementary analysis Found/calc. | |
|---|---|---|---|---|
| [quinoline-6-yl (S)-3-hydroxy-ethyl ester structure] | 93 | Cyclohexane | C<br>H<br>N | 68.47/68.56<br>6.29/6.16<br>5.89/5.71 |

Example 19

Reduction method: A
e.e. of the product after crystallization: >98%
Strain: *Pichia wickerhamii* (IFO 1278)

| Product | Yield % of the theory | Solvent of crystallization | Elementary analysis Found/calc. | |
|---|---|---|---|---|
| [quinoline-7-yl (S)-3-hydroxy-isopropyl ester structure] | 94 | Heptane/acetic acid ethyl ester | C<br>H<br>N | 69.37/69.48<br>6.78/6.61<br>5.27/5.40 |

Example 20

Reduction method: C
e.e. of the product after crystallization: >98%
Literature: R. Noyori, Acc. Res. 1997, 30, 97-102
K. Murata, JOC 1999, 64, 2186-2187

| Product | Yield % of the theory | Solvent of crystallization | Elementary analysis Found/calc. | |
|---|---|---|---|---|
| [structure: 3-methylisoquinoline with ethyl 3-hydroxypropanoate group] | 95 | Cyclohexane | C<br>H<br>N | 69.61/69.48<br>6.84/6.61<br>5.27/5.40 |

Example 21

Reduction method: B/Ru—(R)-MeO-Bipheg (catalyst)
Solvent: EtOH
Pressure: atmospheric pressure $H_2$
Temperature: 50° C.
Reaction time: 50 hours
e.e, of the product after crystallization: >98%
Literature: Tetrahedron Letters, vol. 36, No. 27, 4801-4804

| Product | Yield % of the theory | Solvent of crystallization | Elementary analysis Found/calc. | |
|---|---|---|---|---|
| [structure: 1-methylisoquinoline with tert-butyl 3-hydroxypropanoate group] | 96 | Cyclohexane | C<br>H<br>N | 70.91/71.06<br>7.48/7.37<br>4.93/4.87 |

Example 22

Reduction method: B/Ru—(R)-MeO-BIHEP (catalyst)
Solvent: MeOH
Pressure: 10 bar
Temperature: 80° C.
Reaction time: 40 hours
e.e. of the product after crystallization: >98%
Literature: Tetrahedron, 57 (2001), 2563-2568

| Product | Yield % of the theory | Solvent of crystallization | Elementary analysis Found/calc. | |
|---|---|---|---|---|
| [structure: 3-methylisoquinoline with ethyl 3-hydroxypropanoate group at 7-position] | 95 | Cyclohexane | C<br>H<br>N | 69.57/69.48<br>6.75/6.61<br>5.28/5.40 |

Example 23

Reduction method: B
Solvent: EtOH
Pressure: 50 bar
Temperature: 60° C.
Reaction time: 18 hours
e.e. of the product after crystallization: >99%
Literature: Angewandte Chemie 1999, 111, page 3397

| Product | Yield % of the theory | Solvent of crystallization | Elementary analysis Found/calc. | |
|---|---|---|---|---|
| (1-methylbenzimidazol-5-yl)-CH(OH)-CH₂-C(O)-OMe | 93 | Cyclohexane/ MTBE | C<br>H<br>N | 61.68/61.53<br>6.10/6.02<br>11.87/11.96 |

Example 24

Reduction method: B
Solvent: methanol
Pressure: 120 psi
Temperature: 60° C.
Reaction time: 18 hours
e.e. of the product after crystallization:
Literature: see example 17

| Product | Yield % of the theory | Solvent of crystallization | Elementary analysis Found/calc. | |
|---|---|---|---|---|
| (1-methylbenzimidazol-6-yl)-CH(OH)-CH₂-C(O)-OEt | 94 | Cyclohexane | C<br>H<br>N | 62.99/62.89<br>6.71/6.50<br>11.13/11.28 |

Example 25

Reduction method: B
Solvent: ethanol
Pressure: 1300 psi
Temperature: 60° C.
Reaction time: 24 hours
e.e. of the product after crystallization: >99%
Literature: see example 17

| Produkt | Yield % of the theory | Solvent of crystallization | Elementary analysis Found/calc. | |
|---|---|---|---|---|
| (2-methylbenzoxazol-5-yl)-CH(OH)-CH₂-C(O)-OEt | 96 | Cyclohexane | C<br>H<br>N | 62.57/62.64<br>6.19/6.07<br>5.49/5.62 |

Example 26

Reduction method: C
e.e. of the product after crystallization: >98%
Literature: R. Noyori, Acc. Res. 1997, 30, 97-102
K. Murata, JOC 1999, 64, 2186-2187

| Product | Yield % of the theory | Solvent of crystallization | Elementary analysis Found/calc. | |
|---|---|---|---|---|
| 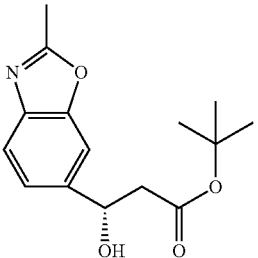 | 94 | Cyclohexane/ acetic acid ethyl ester | C<br>H<br>N | 64.91/64.97<br>7.05/6.91<br>4.98/5.05 |

Example 27

Reduction method: A
e.e. of the product after crystallization: >99%
Strain: *Pichia wickerhamii* (IFO 1278)

| Product | Yield % of the theory | Solvent of crystallization | Elementary analysis Found/calc. | |
|---|---|---|---|---|
| 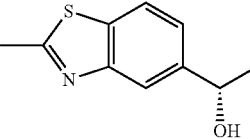 | 95 | Hexane | C<br>H<br>N<br>S | 58.81/58.85<br>5.85/5.70<br>5.17/5.28<br>11.93/12.08 |

Example 28

Reduction method: A
e.e. of the product after crystallization: >99° A)
Strain: *Pichia wickerhamii* (IFO 1278)

| Product | Yield % of the theory | Solvent of crystallization | Elementary analysis Found/calc. | |
|---|---|---|---|---|
| 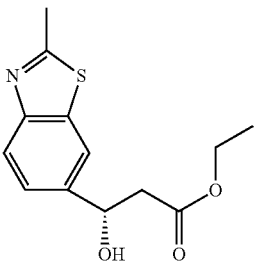 | 94 | Cyclohexane | C<br>H<br>N<br>S | 58.94/58.85<br>5.85/5.70<br>5.17/5.28<br>11.93/12.08 |

Example 29

Reduction method: C
e.e. of the product after crystallization: >98%
Literature: R. Noyori, Acc. Res. 1997, 30, 97-102
K. Murata, JOC 1999, 64, 2186-2187

| Product | Yield % of the theory | Solvent of crystallization | Elementary analysis Found/calc. | |
|---|---|---|---|---|
| (benzothiazole-phenyl-CH(OH)-CH2-C(O)-O-ethyl) | 94 | Hexane | C<br>H<br>N<br>S | 57.28/57.35<br>5.35/5.21<br>5.48/5.57<br>12.63/12.76 |

Example 30

Reduction method: B
Solvent: Me OH
Pressure: 50 bar
Temperature: 50° C.
Reaction time: 24 hours
e.e. of the product after crystallization: >99%
Literature: see example 23

| Product | Yield % of the theory | Solvent of crystallization | Elementary analysis Found/calc. | |
|---|---|---|---|---|
| (benzothiazole-phenyl-CH(OH)-CH2-C(O)-O-methyl) | 96 | Cyclohexane | C<br>H<br>N<br>S | 55.67/55.68<br>4.80/4.67<br>5.95/5.90<br>13.40/13.51 |

The aforementioned compounds of general formula I of examples 16 to 30 all form part of the subject matter of the present invention.

The use of the novel intermediate products according to the invention for the preparation of epothilone intermediates known in literature is shown in the following examples:

General Specification for the Preparation of the TBDMS Ethers (Intermediate Compounds from WO 00/66589, Schering Ag)

100 mmole of the hydroxy ester of the general formula (I) and 150 mmole of imidazole are dissolved in 150 ml of dimethylformamide and 125 mmole of tert. butyl dimethylsilyl chloride (TBDMS-Cl) are added at 0° C. Stirring is carried out at room temperature for 12 hours. 70 mmole of methanol are added to destroy the excess of TBDMS-Cl and stirring is carried out at room temperature for further 2 hours. 5 ml of water and 50 ml of n-hexane are added and vigorous stirring is carried out for 10 minutes. The hexane phase is separated and rejected. 1000 ml of water is added to the DMF phase and extraction is carried out twice with 150 ml acetic acid ethyl ester each. The combined organic phases are separated and concentrated to dryness in vacuo.

It proved to be advantageous in the case of a consecutive reaction with DIBAH or DIBAH/BuLi to extract with dichloromethane or toluene and to carry out the further reaction directly with the solution.

Example 31

| Product | Yield % of the theory | Solvent for extraction | Elementary analysis Found/calc. | |
|---|---|---|---|---|
| (isoquinoline-CH(OTBDMS)-CH2-C(O)-O-ethyl) | 99 | Acetic acid ethyl ester | C<br>H<br>N<br>Si | 66.93/66.81<br>8.30/8.13<br>3.76/3.90<br>7.67/7.81 |

Example 32

| Product | Yield % of the theory | Solvent for extraction | Elementary analysis Found/calc. | |
|---|---|---|---|---|
| 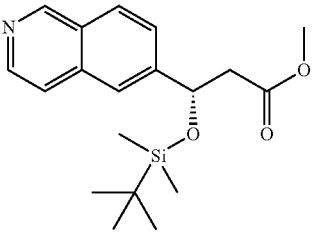 | 98 | Dichloromethane | C<br>H<br>N<br>Si | 65.93/66.05<br>7.97/7.88<br>3.92/4.05<br>8.01/8.13 |

Example 33

| Product | Yield % of the theory | Solvent for extraction | Elementary analysis Found/calc. | |
|---|---|---|---|---|
| 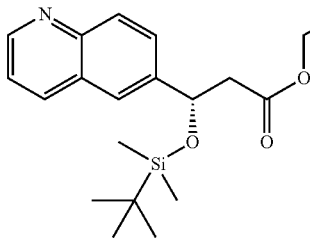 | 99 | Toluene | C<br>H<br>N<br>Si | 66.93/66.81<br>8.27/8.13<br>3.76/3.90<br>7.67/7.81 |

Example 34

| Product | Yield % of the theory | Solvent for extraction | Elementary analysis Found/calc. | |
|---|---|---|---|---|
| 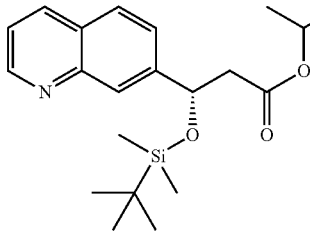 | 98 | Acetic acid ethyl ester | C<br>H<br>N<br>Si | 67.69/67.52<br>8.51/8.36<br>3.67/3.75<br>7.34/7.52 |

Example 35

| Product | Yield % of the theory | Solvent for extraction | Elementary analysis Found/calc. | |
|---|---|---|---|---|
| 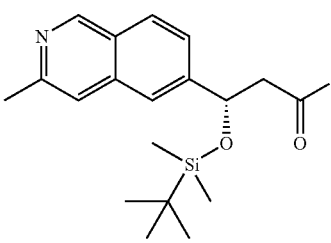 | 99 | Acetic acid ethyl ester | C<br>H<br>N<br>Si | 67.65/67.52<br>8.45/8.36<br>3.68/3.75<br>7.43/7.52 |

Example 36

| Product | Yield % of the theory | Solvent for extraction | Elementary analysis Found/calc. | |
|---|---|---|---|---|
| (structure) | 100 | Dichloromethane | C<br>H<br>N<br>Si | 68.91/68.78<br>8.87/8.78<br>3.35/3.49<br>6.87/6.99 |

Example 37

| Product | Yield % of the theory | Solvent for extraction | Elementary analysis Found/calc. | |
|---|---|---|---|---|
| (structure) | 99 | Acetic acid ethyl ester | C<br>H<br>N<br>Si | 67.65/67.52<br>8.43/8.36<br>3.68/3.75<br>7.48/7.52 |

Example 38

| Product | Yield % of the theory | Solvent for extraction | Elementary analysis Found/calc. | |
|---|---|---|---|---|
| (structure) | 98 | Acetic acid ethyl ester | C<br>H<br>N<br>Si | 62.12/62.03<br>8.30/8.10<br>7.92/8.04<br>7.94/8.06 |

Example 39

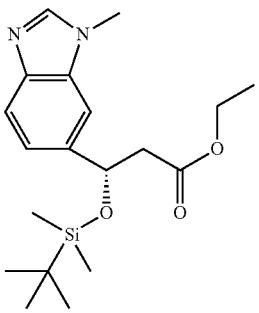

| Product | Yield % of the theory | Solvent for extraction | Elementary analysis Found/calc. | |
|---|---|---|---|---|
| (structure) | 99 | Toluene | C | 63.09/62.95 |
| | | | H | 8.43/8.34 |
| | | | N | 7.65/7.73 |
| | | | Si | 7.65/7.75 |

Example 40

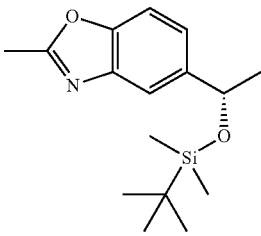

| Product | Yield % of the theory | Solvent for extraction | Elementary analysis Found/calc. | |
|---|---|---|---|---|
| (structure) | 99 | Toluene | C | 62.87/62.78 |
| | | | H | 8.16/8.04 |
| | | | N | 3.76/3.85 |
| | | | Si | 7.65/7.73 |

Example 41

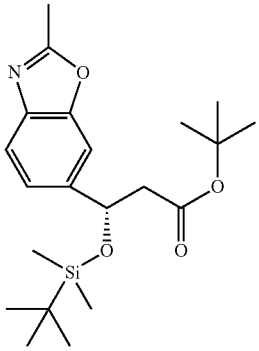

| Product | Yield % of the theory | Solvent for extraction | Elementary analysis Found/calc. | |
|---|---|---|---|---|
| (structure) | 100 | Dichloromethane | C | 64.61/64.41 |
| | | | H | 8.62/8.49 |
| | | | N | 3.45/3.58 |
| | | | Si | 7.03/7.17 |

Example 42

| Product | Yield % of the theory | Solvent for extraction | Elementary analysis Found / calc. | |
|---|---|---|---|---|
| 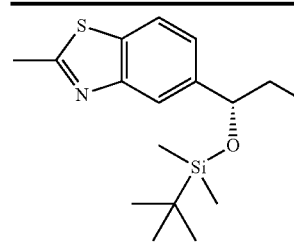 | 99 | Acetic acid ethyl ester | C<br>H<br>N<br>S<br>Si | 60.23/60.12<br>7.82/7.70<br>3.57/3.69<br>8.34/8.45<br>7.30/7.40 |

Example 43

| Product | Yield % of the theory | Solvent for extraction | Elementary analysis Found/calc. | |
|---|---|---|---|---|
| 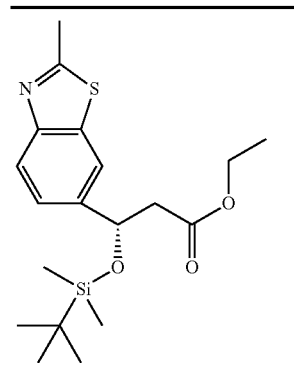 | 99 | Acetic acid ethyl ester | C<br>H<br>N<br>S<br>Si | 60.26/60.12<br>7.85/7.70<br>3.59/3.69<br>8.33/8.45<br>7.31/7.40 |

Example 44

50

| Product | Yield % of the theory | Solvent for extraction | Elementary analysis Found/calc. | |
|---|---|---|---|---|
| 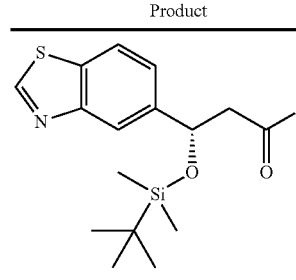 | 98 | Dichloromethane | C<br>H<br>N<br>S<br>Si | 59.23/59.14<br>7.51/7.44<br>3.72/3.83<br>8.66/8.77<br>7.60/7.68 |

Example 45

| Product | Yield % of the theory | Solvent for extraction | Elementary analysis Found/calc. | |
|---|---|---|---|---|
| 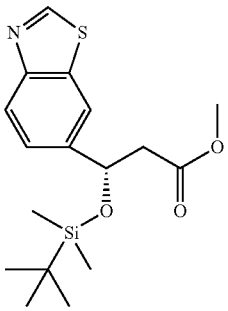 | 98 | Dichloromethane | C<br>H<br>N<br>S<br>Si | 59.15/59.08<br>7.25/7.17<br>3.87/3.98<br>9.01/9.12<br>7.88/7.99 |

General Production Specification for the Reduction of the Silyl Esters (Intermediate Stages from U.S. Pat. No. 6,387,927 and PCT/EP99110129, NOVARTIS)

20 ml of a 1 M solution of DIBAH in dichloromethane are added dropwise at −78° C. (under nitrogen) for 30 minutes to a solution of silyl ester, 10 mmole, dissolved in 100 ml of dichloromethane, which was produced in examples 31 to 46 (with the exception of the tert. butyl esters). Stirring is carried out for 3 hours at −78° C. Further 5 ml of DIBAH solution are added and stirring is continued for further 2 hours. 6 ml of methanol are added dropwise and the mixture is allowed to reach room temperature. 50 ml of dichloromethane and 50 ml of water are added and the suspension is filtered over Celite. The organic phase is separated, washed with water and concentrated to dryness in vacuo.

Example 46

| Product | Yield % of the theory | Elementary analysis Found/calc. | |
|---|---|---|---|
| 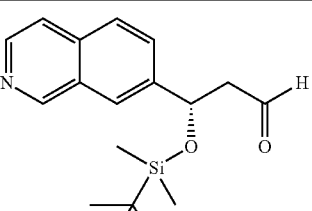 | 97 | C<br>H<br>N<br>Si | 68.65/68.53<br>8.12/7.99<br>4.31/4.44<br>8.75/8.90 |

Example 47

| Product | Yield % of the theory | Elementary analysis Found/calc. | |
|---|---|---|---|
| 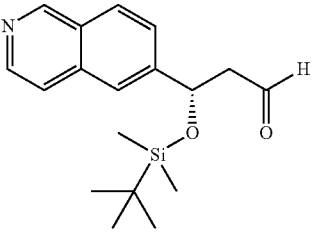 | 98 | C<br>H<br>N<br>Si | 68.62/68.53<br>8.09/7.99<br>4.32/4.44<br>8.80/8.90 |

Example 48

| Product | Yield % of the theory | Elementary analysis Found/calc. | |
|---|---|---|---|
| 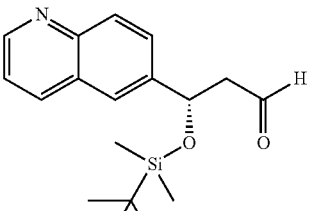 | 96 | C<br>H<br>N<br>Si | 68.60/68.53<br>8.11/7.99<br>4.31/4.44<br>8.82/8.90 |

Example 49

| Product | Yield % of the theory | Elementary analysis Found/calc. |
|---|---|---|
|  | 98 | C 68.62/68.53<br>H 8.14/7.99<br>N 4.36/4.44<br>Si 8.81/8.90 |

Example 50

| Product | Yield % of the theory | Elementary analysis Found/calc. |
|---|---|---|
| 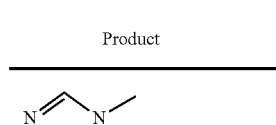 | 97 | C 69.32/69.26<br>H 8.41/8.26<br>N 4.12/4.25<br>Si 8.44/8.52 |

Example 51

| Product | Yield % of the theory | Elementary analysis Found/calc. |
|---|---|---|
| 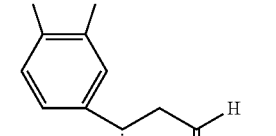 | 96 | C 69.35/69.26<br>H 8.40/8.26<br>N 4.17/4.25<br>Si 8.40/8.52 |

Example 52

| Product | Yield % of the theory | Elementary analysis Found/calc. |
|---|---|---|
| 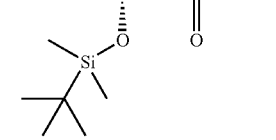 | 98 | C 64.15/64.11<br>H 8.34/8.23<br>N 8.67/8.80<br>Si 8.69/8.82 |

Example 53

| Product | Yield % of the theory | Elementary analysis Found/calc. |
|---|---|---|
| 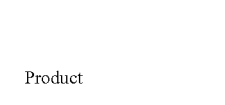 | 97 | C 64.19/64.11<br>H 8.37/8.23<br>N 8.64/8.80<br>Si 8.66/8.82 |

Example 54

| Product | Yield % of the theory | Elementary analysis Found/calc. |
|---|---|---|
|  | 96 | C 63.99/63.91<br>H 8.01/7.89<br>N 4.34/4.38<br>Si 8.68/8.79 |

Example 55

| Product | Yield % of the theory | Elementary analysis Found/calc. | |
|---|---|---|---|
| 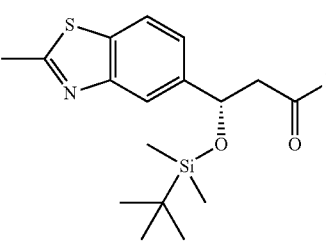 | 98 | C<br>H<br>N<br>S<br>Si | 60.93/60.85<br>7.66/7.51<br>4.08/4.17<br>9.44/9.56<br>8.25/8.37 |

Example 56

| Product | Yield % of the theory | Elementary analysis Found/calc. | |
|---|---|---|---|
| 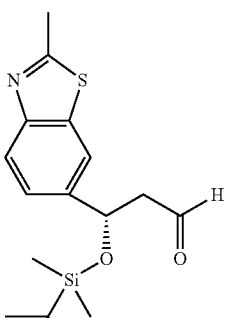 | 97 | C<br>H<br>N<br>S<br>Si | 60.96/60.85<br>7.68/7.51<br>4.09/4.17<br>9.47/9.56<br>8.27/8.37 |

Example 57

| Product | Yield % of the theory | Elementary analysis Found/calc. | |
|---|---|---|---|
| 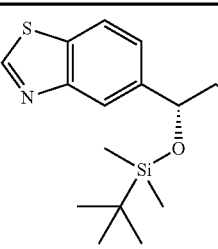 | 96 | C<br>H<br>N<br>S<br>Si | 59.85/59.77<br>7.34/7.21<br>4.27/4.36<br>9.88/9.97<br>8.66/8.74 |

Example 58

| Product | Yield % of the theory | Elementary analysis Found/calc. | |
|---|---|---|---|
| 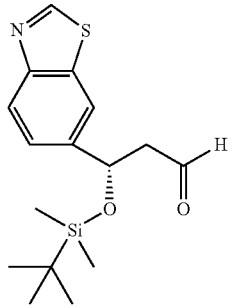 | 97 | C<br>H<br>N<br>S<br>Si | 59.88/59.77<br>7.32/7.21<br>4.28/4.36<br>9.86/9.97<br>8.69/8.74 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 103 61 794.9, filed Dec. 31, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of a compound of formula I,

wherein:

A is a bicyclic heteroaromatic residue of formula

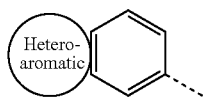

wherein "heteroaromatic" stands for a 5- or 6-membered heteroaromatic ring having up to 2 heteroatoms selected from oxygen, nitrogen or sulphur, which is optionally substituted with one or two substituents selected from alkyl, optionally protected hydroxyalkyl, halo-alkyl, halogen or CN, and R is a straight-chain or branched, optionally saturated alkyl chain, which optionally contains 1-3 oxygen atoms; phenyl; cyclohexyl; or benzyl residue, comprising subjecting a β-ketoester of formula IV

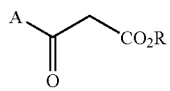
(IV)

to a chemical or microbiological reaction converting the oxo group of formula II to the hydroxyl group of Formula I.

2. A process according to claim 1, wherein R is methyl or ethyl.

3. A process according to claim 1, wherein A is one of the following residues:

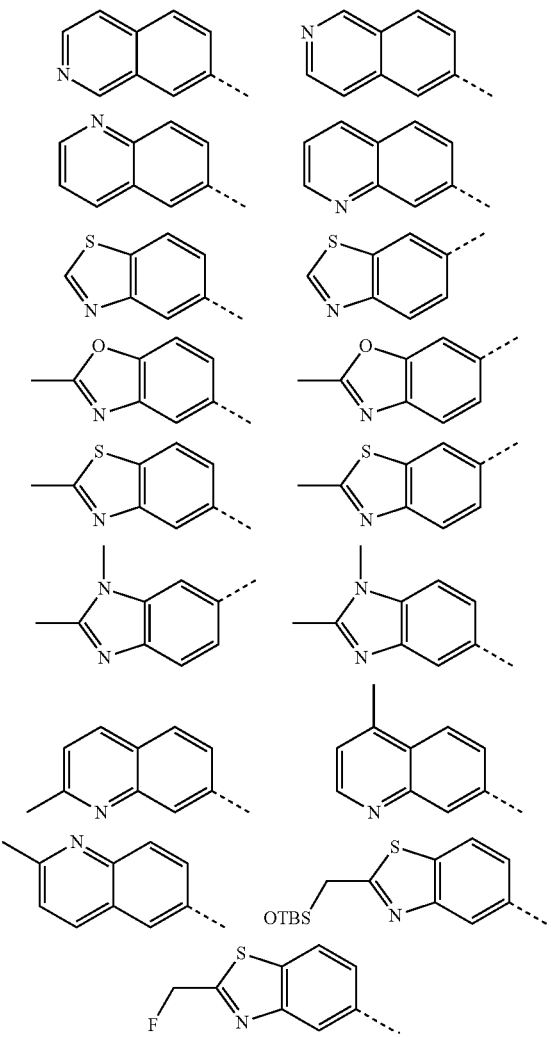

4. A process according to claim 1, wherein A is:

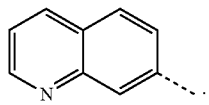

5. A process according to claim 1, wherein A is e:

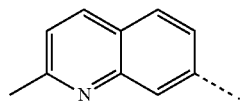

6. A process according to claim 1, wherein A is:

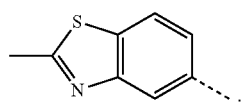

7. A process as claimed in claim 1, wherein the chemical reduction is carried out by means of an asymmetric reduction with a chiral metal catalyst.

8. A process as claimed in claim 1, comprising carrying out a microbiogical reaction by means of an asymmetric reduction with a microorganism of the species baker's yeast, *Brettanomyces bruxellensis*, *Candida albicans*, *Candida boidinii*, *Candida gropengiesseri*, *Candida guilliermondii*, *Candida kefyr*, *Candida pini*, *Candida rugosa*, *Candida solani*, *Candida tropicalis*, *Candida utilis*, *Candida valida*, *Clostridium beijerinckii*, *Clostridium pasteurianum*, *Cryptococcus laurentii*, *Cryptococcus macerans*, *Debaryomyces hansenii*, *Debaryomyces kloeckeri*, *Debaryomyces nicotianae*, *Debaryomyces vini*, *Endomycopsis fibuliger*, *Hanseniaspora guilliermondii*, *Hanseniaspora osmophila*, *Hanseniaspora uvarum*, *Hansenula capsulata*, *Hansenula holstii*, *Hansenula polymorpha*, *Hansenula saturnus*, *Hansenula silvicola*, *Issatchenkia orientalis*, *Kloeckera apiculata*, *Kloeckera corticis*, *Kloeckera javanica*, *Kloeckera* sp., *Kluyveromyces lactis*, *Kluyveromyces marxianus Kluveromyces sphaerica*, *Lactobacillus kefir*, *Nadsonia fulvescens*, *Octosporomyces octosporus*, *Pichia anomala*, *Pichia cactophila*, *Pichia farinosa*, *Pichia fermentans*, *Pichia holstii*, *Pichia jadinii*, *Pichia membranaefaciens*, *Pichia pijperi*, *Pichia silvicola*, *Pichia subpelliculosa*, *Pichia wickerhamii*, *Rhodotorula flava*, *Rhodotorula glutinis*, *Rhodotorula minuta* var. *minuta*, *Saccharomyces acidificans*, *Saccharomyces bailii*, *Saccharomyces bayanus*, *Saccharomyces carlsb*. strain *Herrliberg*, *Saccharomyces carlsbergensis*, *Saccharomyces cerevisiae*, *Saccharomyces chevalieri*, *Saccharomyces exiguus*, *Saccharomycopsis fibuligera*, *Saccharomyces paradoxus*, *Saccharomyces pastorianus*, *Saccharomyces pastorianus* formerly *Saccharomycopsis capsularis*, *Saccharomyces* sp., *Schizosaccharomyces pombe*, *Schizosaccharomyces octosporus*, *Sporobolomyces coralliformis*, *Sporobolomyces salmonicolor*, *Torulopsis pinus*, *Trigonopsis varabilis*, *Tremella fuciformis*, *Waltomyces lipofer*, *Zygosaccharomyces fermentati* or *Zygosaccharomyces rouxii*.

9. A process as claimed in claim 8, wherein the microorganism used is *Pichia wickerhamii* (IFO 1278).

* * * * *